(12) United States Patent
Jacobs et al.

(10) Patent No.: US 6,333,002 B1
(45) Date of Patent: Dec. 25, 2001

(54) STERILIZATION PROCESS USING SMALL AMOUNT OF STERILANT TO DETERMINE THE LOAD

(75) Inventors: Paul T. Jacobs, Trabuco Canyon; Szu-Min Lin, Laguna Hills; Jenn-Hann Wang, Mission Viejo, all of CA (US)

(73) Assignee: Ethicon, Inc., New Brunswick, NJ (US)

(*) Notice: Subject to any disclaimer, the term of this patent is extended or adjusted under 35 U.S.C. 154(b) by 0 days.

(21) Appl. No.: 09/223,125

(22) Filed: Dec. 30, 1998

(51) Int. Cl.[7] .............................. G05B 2/00; G01N 33/00
(52) U.S. Cl. ................................................ 422/3; 436/135
(58) Field of Search ..................... 422/3, 22, 28, 422/11, 110, 111, 292, 105, 33, 112, 5, 788, 9, 90, 82.05; 436/135

(56) References Cited

U.S. PATENT DOCUMENTS

| 4,169,123 | 9/1979 | Moore et al. |
|---|---|---|
| 4,169,124 | 9/1979 | Forstrom et al. |
| 4,643,876 | 2/1987 | Jacobs et al. |
| 4,756,882 | 7/1988 | Jacobs et al. |
| 4,908,188 | * 3/1990 | Jefferis, III et al. .................. 422/111 |
| 4,956,145 | 9/1990 | Cummings et al. |
| 5,608,156 | * 3/1997 | Ando et al. .......................... 73/31.06 |
| 5,788,925 | 8/1998 | Pai et al. |
| 5,876,666 | * 3/1999 | Lin et al. ............................... 422/29 |
| 5,882,590 | * 3/1999 | Stewart et al. ........................ 422/28 |
| 5,882,611 | * 3/1999 | Williams et al. ..................... 422/292 |

FOREIGN PATENT DOCUMENTS

| 0 744 615 A3 | 11/1997 | (EP) . |
|---|---|---|
| WO 98/57673 | 12/1998 | (WO) . |

* cited by examiner

Primary Examiner—Robert J. Warden, Sr.
Assistant Examiner—Monzer R. Chorbaji
(74) Attorney, Agent, or Firm—Knobbe, Martens, Olson & Bear, LLP

(57) ABSTRACT

A method for determining and sterilizing a load in a sterilization chamber. A small amount of sterilant is introduced into the sterilization chamber and the concentration of sterilant is measured. The load of equipment to be sterilized is determined from the concentration of sterilant, and more sterilant is added, if necessary, based on the load. The process is repeated, if necessary, until the load is sterilized. The sterilant is preferably hydrogen peroxide, and the concentration of hydrogen peroxide is preferably determined by a spectrophotometric method in the infrared or ultraviolet regions. By monitoring the sterilant concentration and adding more as needed, the equipment in the chamber can be sterilized efficiently without exposing it to high concentrations of sterilant which could damage the equipment or leave too much residual on the equipment.

26 Claims, 10 Drawing Sheets

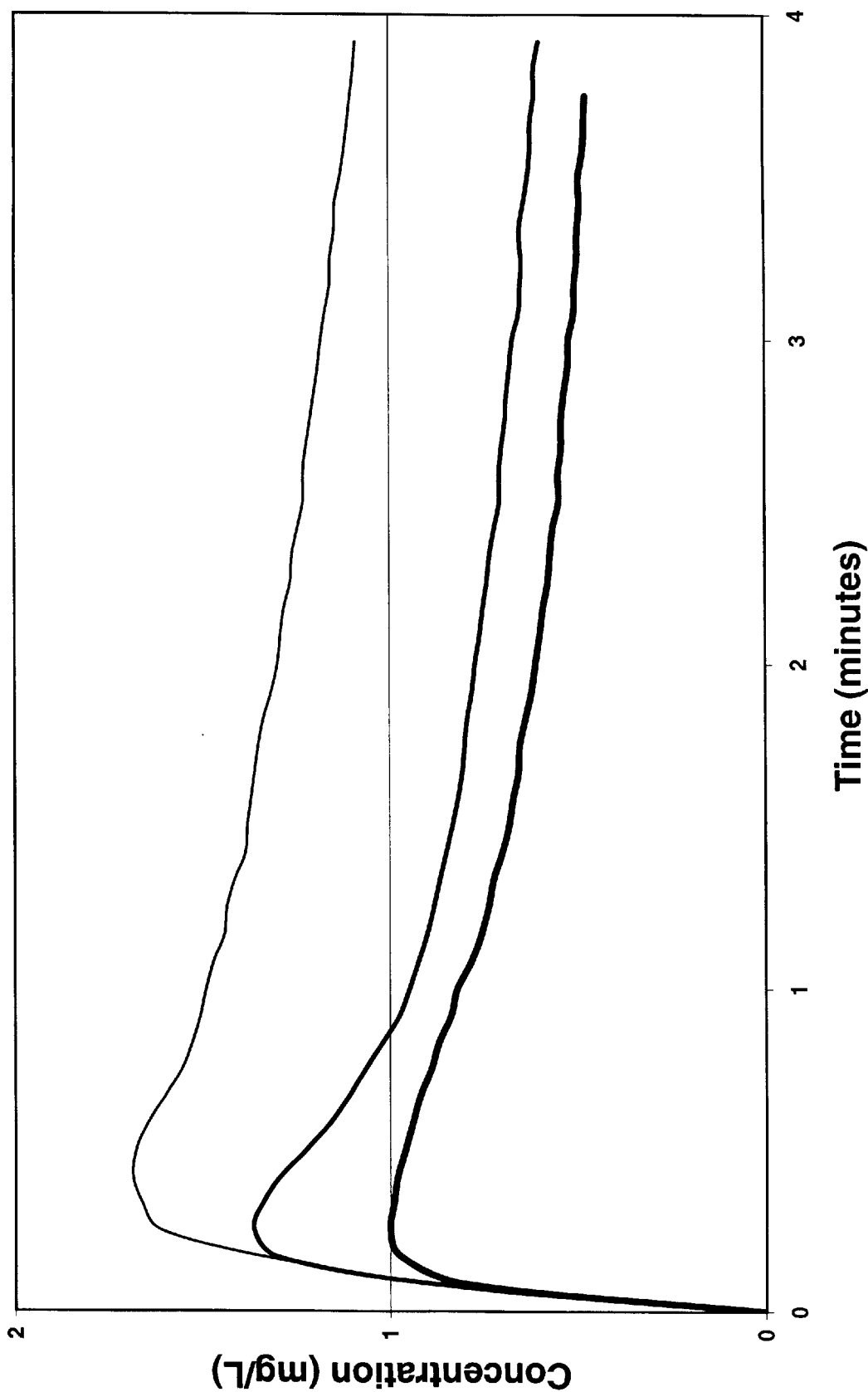

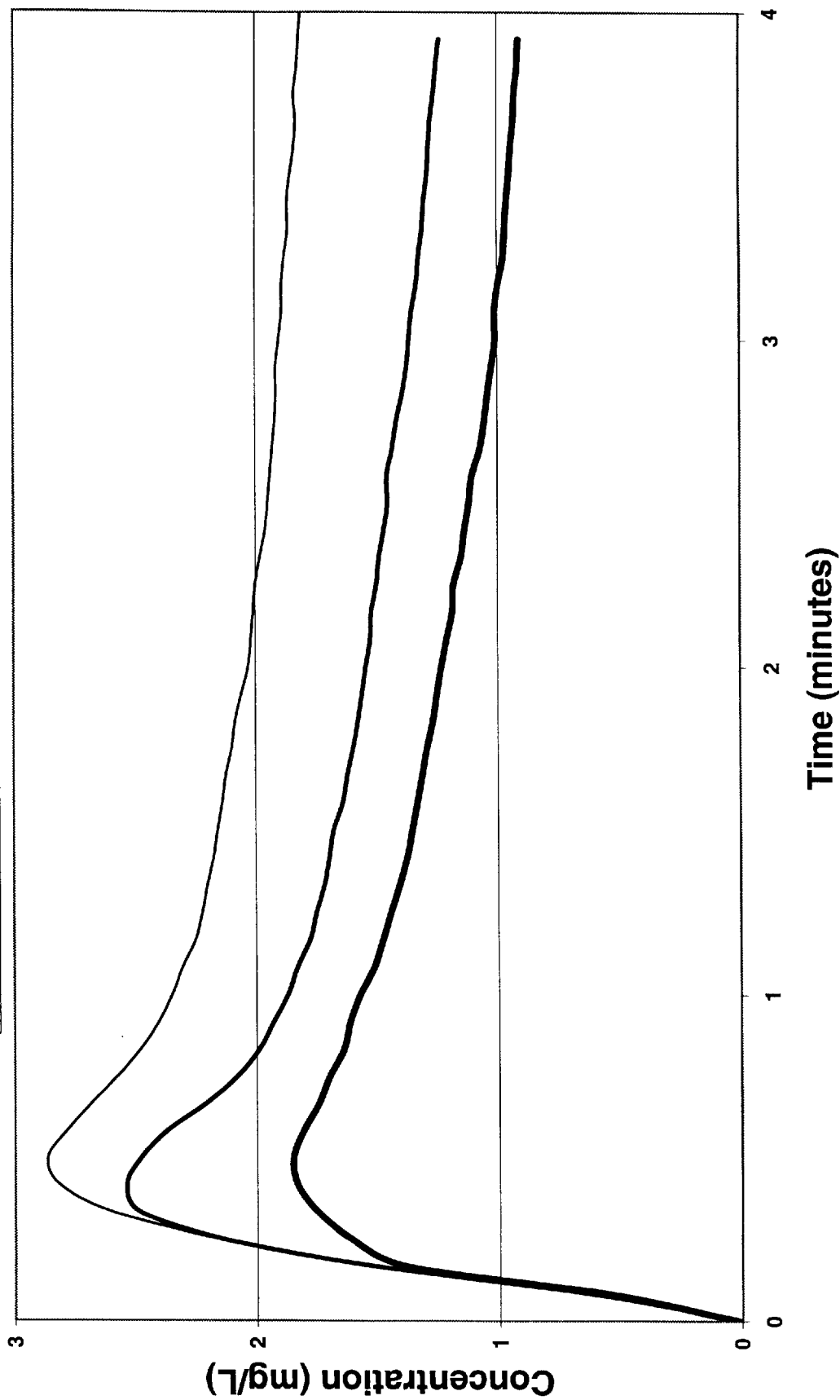

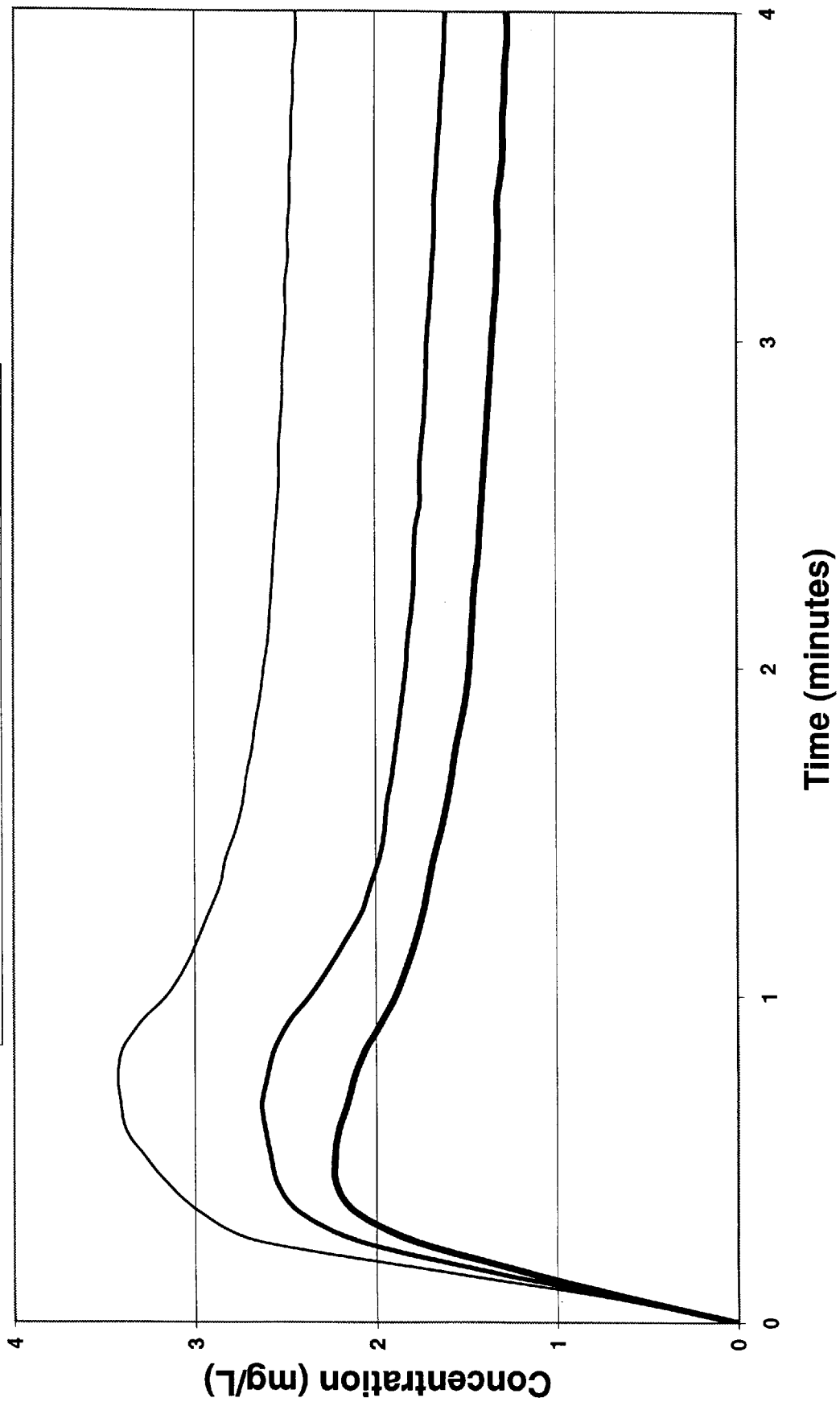

Figure 8A

| | | | More acceptable efficacy and material compatibility | |
|---|---|---|---|---|
| large amount of peroxide (3 grams of 59%) | Less acceptable material compatibility | | | |
| medium amount of peroxide (2 grams of 59%) | | More acceptable efficacy and material compatibility | Less acceptable efficacy | |
| small amount of peroxide (1 gram of 59%) | More acceptable efficacy and material compatibility | | | |
| | Light load (one tray) | Medium load (two trays) | Heavy load (three trays) | |

STERILIZATION PROCESS USING SMALL AMOUNT OF STERILANT TO DETERMINE THE LOAD

FIELD OF THE INVENTION

This invention relates to a sterilization process in which a small amount of sterilant is introduced into the chamber, the concentration of sterilant in the chamber is measured to determine the load, and more sterilant is introduced, if necessary, based on the determined load.

BACKGROUND OF THE INVENTION

Medical instruments have traditionally been sterilized using heat, for example steam, or a chemical, such as formaldehyde or ethylene oxide in the gas or vapor state. Both heat and chemical sterilization have drawbacks. For example, many medical devices, such as fiberoptic devices, endoscopes, power tools, etc. are sensitive to heat, moisture, or both.

Formaldehyde and ethylene oxide are both toxic gases which pose a potential hazard to health workers. After sterilization with ethylene oxide, the articles require long aeration times to remove the gas from articles which have been sterilized. This makes the sterilization cycle time undesirably long.

Sterilization using liquid hydrogen peroxide solutions has been found to require a high concentration of sterilant, extended exposure times and/or elevated temperatures. However, sterilization using hydrogen peroxide vapor has been shown to have some advantages over other chemical sterilization processes (see, for example, U.S. Pat. Nos. 4,169,123 and 4,169,124). The combination of hydrogen peroxide vapor and a plasma provides additional advantages, as disclosed in U.S. Pat. No. 4,643,876. U.S. Pat. 4,756,882 discloses the use of hydrogen peroxide vapor, generated from an aqueous solution of hydrogen peroxide, as a precursor of the reactive species generated by a plasma generator. The combination of hydrogen peroxide vapor in close proximity with the article to be sterilized and plasma acts to sterilize the articles, even in closed packages.

Effective sterilization of articles with hydrogen peroxide vapor, either with or without plasma, requires a certain minimum concentration of hydrogen peroxide vapor. If not enough hydrogen peroxide vapor is present, the article will not be sterilized.

If too much hydrogen peroxide is used, the hydrogen peroxide vapor can potentially damage the medical devices, particularly if they contain nylon, neoprene, brass or copper. For hydrogen peroxide absorbent materials, too much peroxide may leave an unacceptable residue on the medical device that may be incompatible with the user or patient. In addition, the use of too much hydrogen peroxide increases the cost of sterilization.

The determination of the appropriate amount of peroxide is especially important for large sterilizers, because the load in large sterilizers can vary more than the load in small sterilizers. One cannot assume the worst-case scenario for each cycle and introduce the maximum possible amount of sterilant. Therefore, there is a need for a method for determining how much hydrogen peroxide is needed to effectively sterilize the medical device without damaging it or leaving too much residual.

There is a need for determining the load of equipment to be sterilized in the sterilization chamber in order to obtain the best efficiency and material compatibility

SUMMARY OF THE INVENTION

One aspect of the present invention relates to a method of determining and sterilizing a load in a sterilization chamber. The method comprises introducing a known amount of sterilant into the sterilization chamber, measuring a parameter related to the concentration of sterilant in the sterilization chamber, where the parameter is measured during or after introducing the sterilant, determining the load in the sterilization chamber from the concentration of sterilant in the sterilization chamber, where the determining is during or after the measuring, repeating the method, if necessary, and sterilizing the load.

Preferably, the known amount of sterilant is less than or equal to 50% of the amount to sterilize a fully loaded chamber. Advantageously, the known amount of sterilant is an amount which produces a pressure in the chamber less than the vapor pressure of the sterilant. Preferably, the sterilant is introduced from a reservoir of sterilant or from a cassette. Advantageously, the sterilant is introduced from at least one cell in the cassette.

In one embodiment, the parameter is measured over a time period, where the time period is the time during the determining. Advantageously, the sterilant comprises a source of hydrogen peroxide. Preferably, the source of peroxide is a liquid solution or a solid peroxide complex.

Advantageously, the concentration of sterilant is measured by a method selected from a spectrophotometric method, measuring the pressure in the sterilization chamber, or measuring with a semiconductor sensor. Preferably, the parameter related to the concentration of sterilant is measured by a spectrophotometric method in the infrared or ultraviolet region.

In a preferred embodiment, the method additionally comprises exposing the load to plasma. Advantageously, the plasma is generated within the chamber. In an alternative embodiment, the method is performed within the chamber and the plasma is generated in a second, separate chamber, and the plasma is flowed into the sterilization chamber.

In one embodiment, the known amount of sterilant is more than the amount of sterilant required to sterilize said load. Preferably, at least a portion of the sterilant is removed with vacuum.

In another embodiment, the determining and sterilizing further comprise aborting the method. Advantageously, aborting the method comprises removing at least a portion of the sterilant with vacuum. Alternatively, aborting the method comprises decomposing at least a portion of the sterilant with plasma.

Advantageously, the load is determined based on the concentration of sterilant. Preferably, the determining is based on the maximum of the parameter related to the concentration of sterilant in the time period. Alternatively, the determining is based on the minimum of the parameter in the time period. Advantageously, the minimum of the parameter in the time period is measured within four minutes after introducing the known amount of sterilant into the chamber.

In another embodiment, the determining is based on the rate of change of the parameter in the time period from the maximum to the minimum. Preferably, the rate of change of the parameter is measured within four minutes from the time when the known amount is introduced into the chamber. Advantageously, the determining is based on the rate of change of the parameter in the time period from the initial time to the maximum in the parameter.

BRIEF DESCRIPTION OF THE DRAWINGS

FIG. 5 is a graph of the concentration of hydrogen peroxide versus time in a sterilization chamber charged with 1 gram of 59% hydrogen peroxide with three different loadings of equipment to be sterilized.

FIG. 6 is a graph of the concentration of hydrogen peroxide versus time in a sterilization chamber charged with 2 grams of 59% hydrogen peroxide with three different loadings of equipment to be sterilized.

FIG. 7 is a graph of the concentration of hydrogen peroxide versus time in a sterilization chamber charged with 3 grams of 59% hydrogen peroxide with three different loadings of equipment to be sterilized.

FIG. 8A is a diagram showing the dependence of sterilization efficiency and material compatibility as a function of the amount of hydrogen peroxide and the loading of equipment to be sterilized.

DETAILED DESCRIPTION OF THE PREFERRED EMBODIMENT

Figure 1:
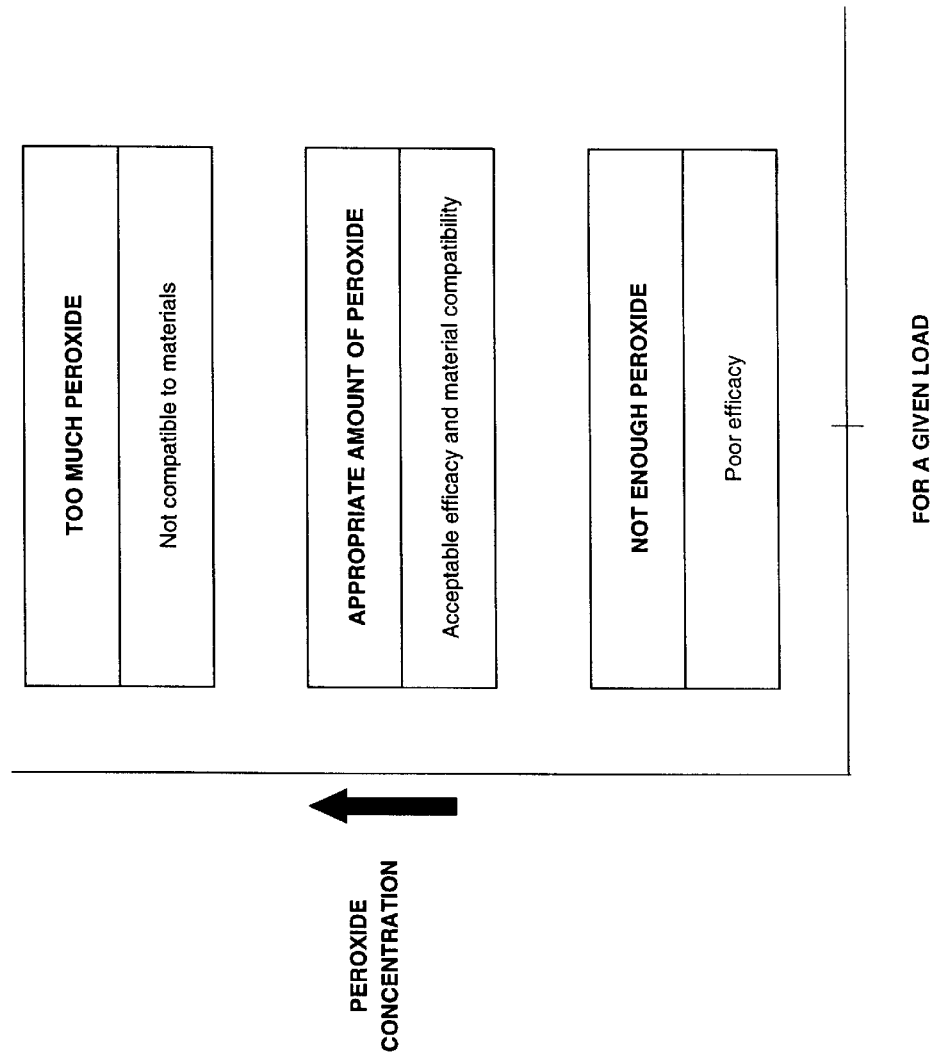
FIG. 1 is a block diagram illustrating the effects of having not enough, an appropriate amount, and too much hydrogen peroxide in a sterilization chamber.

Sterilizing medical devices with hydrogen peroxide vapor requires that the concentration of hydrogen peroxide vapor in the sterilization chamber be high enough to achieve effective sterilization. If too much hydrogen peroxide vapor is used, however, the hydrogen peroxide can damage the medical device or leave too much peroxide residual. Furthermore, use of too much hydrogen peroxide adds to the expense of sterilization.

Even if the concentration of hydrogen peroxide at the start of the sterilization process appears to be high enough to sterilize the equipment in the sterilization chamber, the equipment in the sterilization chamber may absorb or decompose enough hydrogen peroxide to make the sterilization process ineffective. It is difficult to determine how much hydrogen peroxide should be added to a sterilization process, because the amount of needed hydrogen peroxide depends on the temperature, exposure time, and the load in the sterilization chamber. The load is determined not only by the quantity of medical devices but also by what type of medical devices are present and by how much hydrogen peroxide is absorbed or decomposed by the devices.

In one embodiment of the method of the present invention, enough hydrogen peroxide to sterilize a possible light load of medical devices is injected into the sterilization chamber, and the concentration of hydrogen peroxide is monitored as a function of time. If the concentration of hydrogen peroxide as measured by the monitor falls to the point that the sterilization will not be effective, more hydrogen peroxide is added.

The method is particularly important with large sterilization chambers, because the amount of equipment that can be placed in a small sterilization chamber is limited. In the smaller sterilization chamber, the "normal" amount of peroxide is generally acceptable for both efficacy and material compatibility.

A large sterilization chamber can hold multiple loads. If only one tray of devices is placed in the sterilization chamber, the "normal" amount of hydrogen peroxide might be enough to sterilize the devices in the sterilization chamber.

If two or more trays are loaded into the sterilization chamber, two or even three times as much hydrogen peroxide might be required to sterilize the medical equipment in the chamber. If one adds enough hydrogen peroxide to be "safe", depending on the load, too much hydrogen peroxide may be injected into the sterilization chamber, and the process may be incompatible with the medical devices in the chamber.

Although the description of the method has been limited to hydrogen peroxide thus far, the method is also applicable to other sterilants such as peracetic acid and ethylene oxide. Hydrogen peroxide is preferred.

The source of hydrogen peroxide can be a solution of hydrogen peroxide, condensed vapor, or a solid peroxide complex.

Both efficacy and material compatibility are highly dependent on the concentration of peroxide, the exposure time, the exposure temperature, and the load in the chamber. In order to study the effect of load on the concentration of peroxide, the following examples are presented based on the same parameters except the load and the amount of peroxide used. By varying the load and fixing all of the other parameters, the effect of the load on the concentration of peroxide can be easily studied. Also, one, two and three trays which contain the same equipment were used to represent a "light load", "medium load", and "heavy load", respectively.

FIG. 1 shows the effects of varying amounts of peroxide on sterilization efficiency and material compatibility. If not enough peroxide is present in the sterilization chamber, the sterilization efficiency is poor.

If there is too much hydrogen peroxide in the sterilization chamber, the hydrogen peroxide can be incompatible with the materials of the medical device.

If there is an appropriate amount of hydrogen peroxide in the sterilization chamber, the sterilization efficiency is acceptable, and the materials are compatible with the concentration of hydrogen peroxide which is present in the chamber. Having an appropriate amount of hydrogen peroxide in the sterilization chamber is a desirable situation but is difficult to achieve in practice, particularly with large sterilization chambers.

Figure 2:
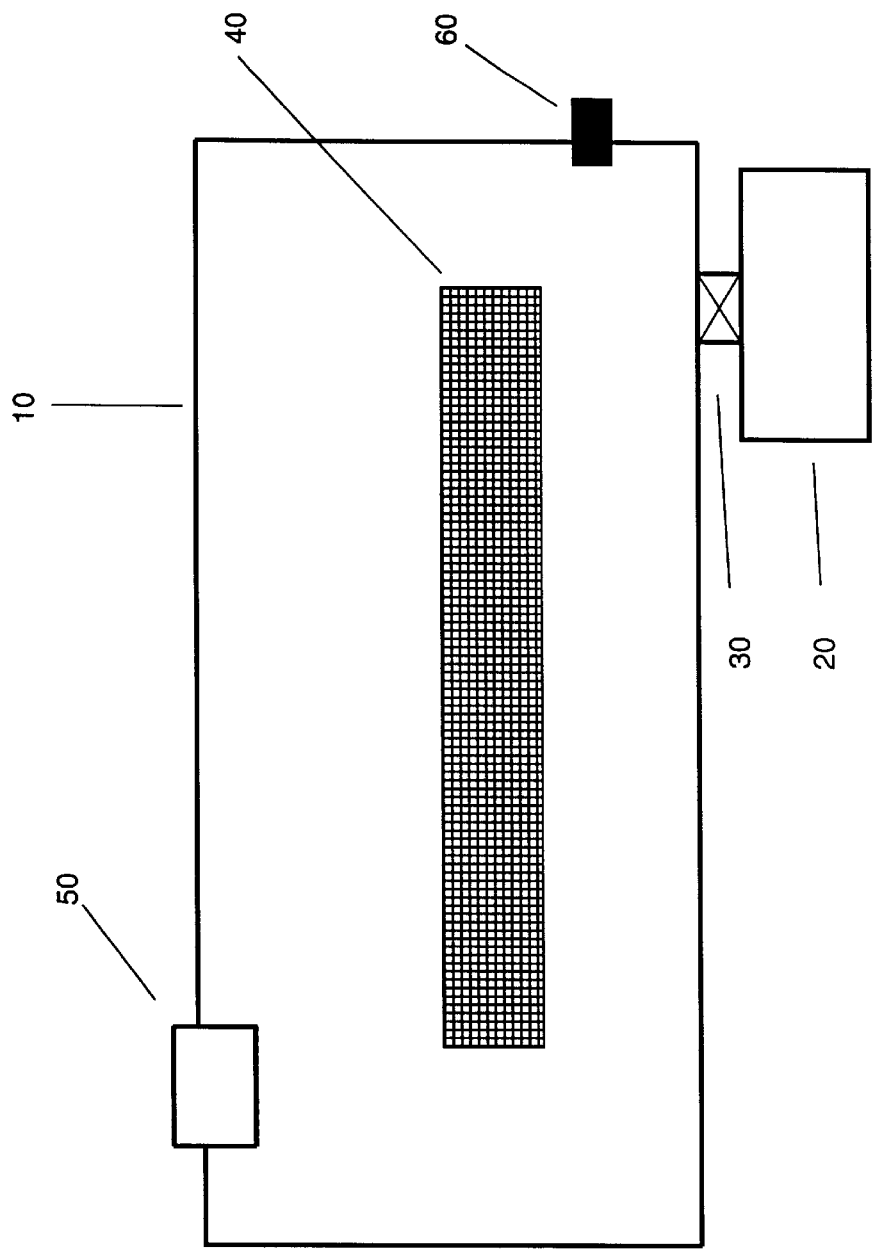
FIG. 2 is an illustration of a sterilization chamber with a light load to be sterilized.

FIG. 2 shows a sterilization chamber with a light load. A sterilization chamber 10 is attached to a vacuum pump 20 through a valve 30. A tray 40 with medical equipment has been placed inside the sterilization chamber. Liquid peroxide is placed inside a vaporizer 50 fluidly attached to the sterilization chamber, so that peroxide vapor can diffuse into the chamber. A peroxide monitor 60 monitors the concentration of hydrogen peroxide in the sterilization chamber as a function of time.

Figure 3:
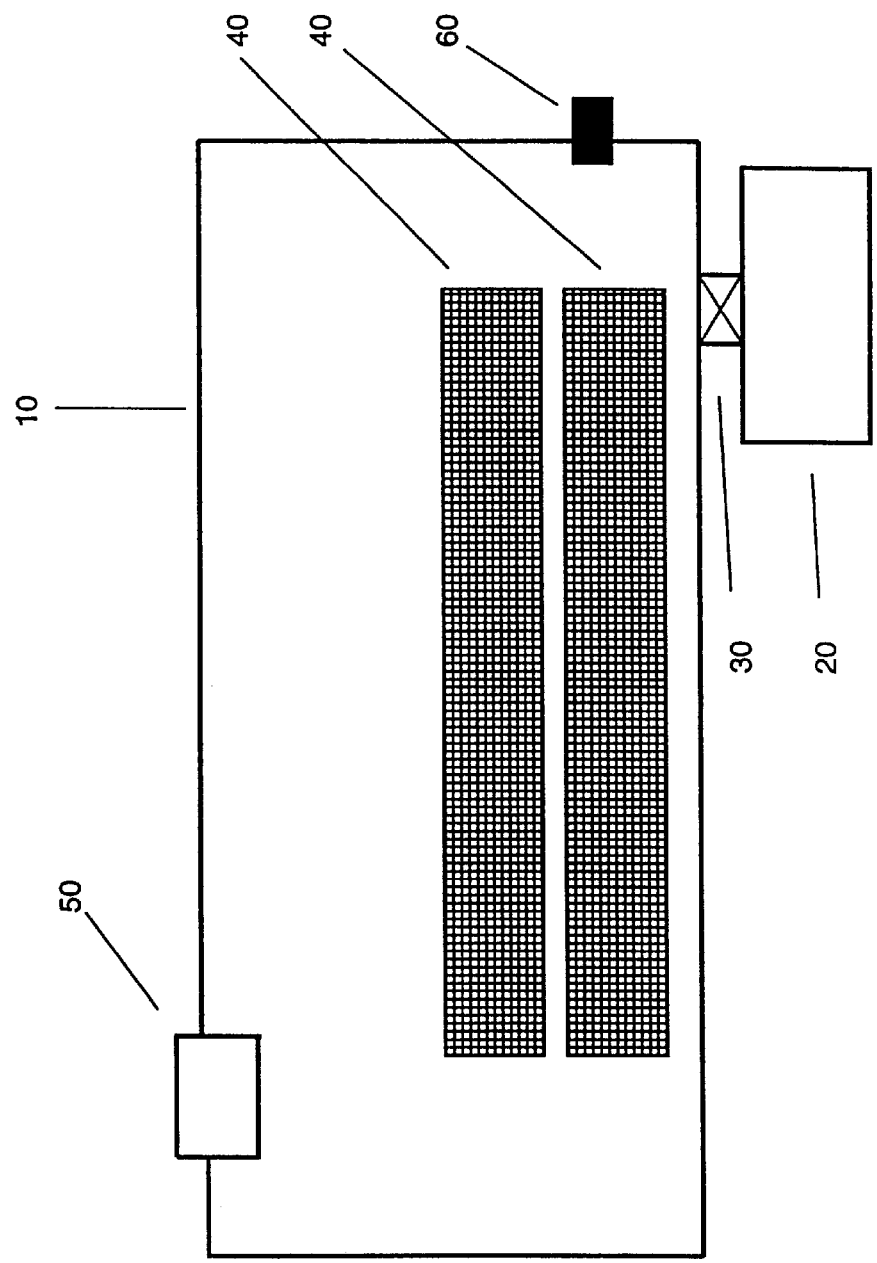
FIG. 3 is an illustration of a sterilization chamber with a medium load to be sterilized.
Figure 4:
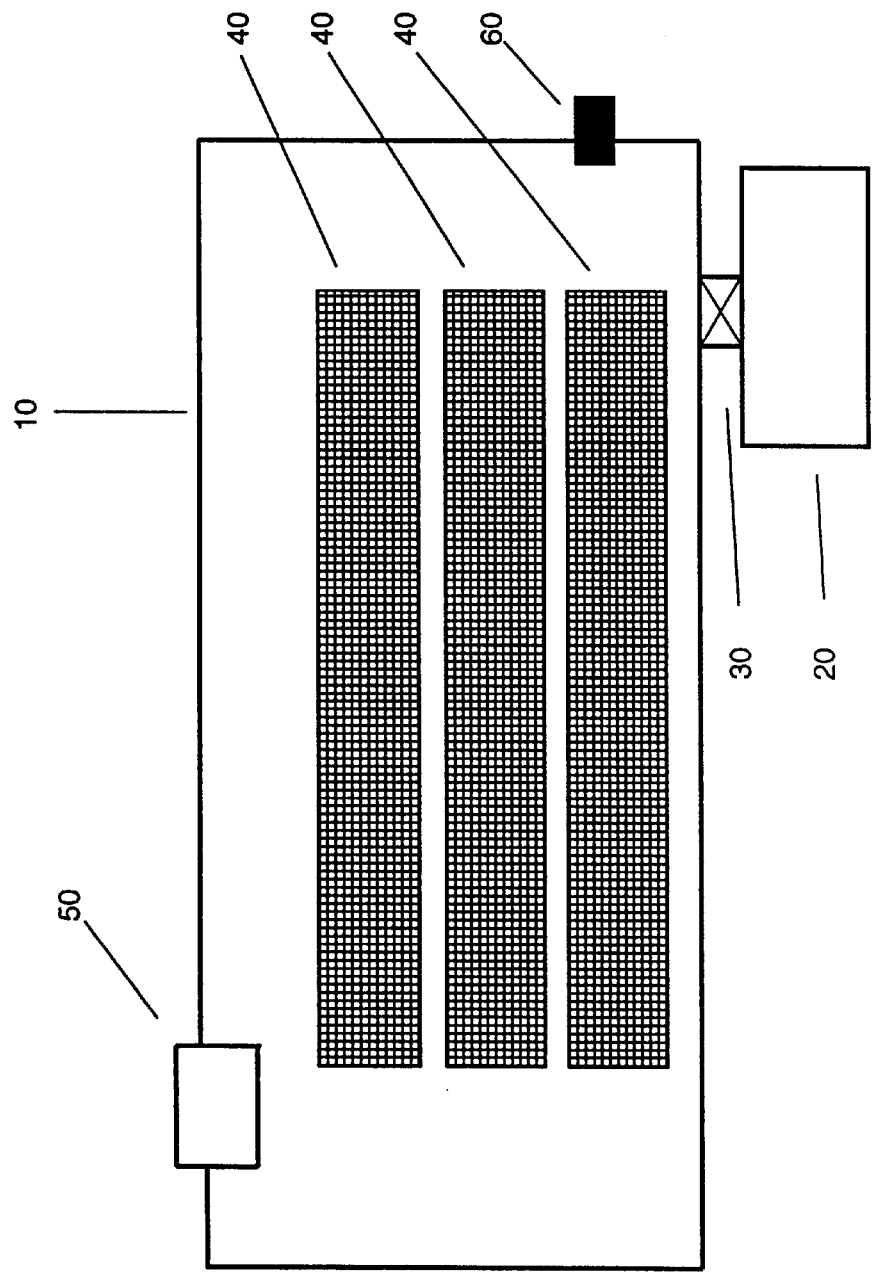
FIG. 4 is an illustration of a sterilization chamber with a heavy load to be sterilized.

FIG. 3 is similar to FIG. 2, except two trays 40 have been placed inside the sterilization chamber. FIG. 4 similarly shows a sterilization chamber with three trays 40.

A typical sterilization process is as follows. The tray with medical equipment is placed in the sterilization chamber, and the chamber is evacuated with the vacuum pump. The liquid peroxide, typically aqueous hydrogen peroxide with a concentration of approximately 59 wt %, is injected into the heated vaporizer at approximately 65° C. The water and peroxide vaporize from the vaporizer and diffuse into the sterilization chamber, thereby contacting and sterilizing the medical equipment in the tray. Although the temperature inside the sterilization chamber can vary, it is generally approximately 45° C. Plasma may optionally be generated with an electrode (not shown) to aid the sterilization process.

The concentration of the hydrogen peroxide vapor in the chamber is preferably monitored with the peroxide monitor. The hydrogen peroxide monitor can utilize any monitoring method that is rapid enough to determine the hydrogen peroxide concentration so that the results are available on a real-time basis, or at least with a very short time delay. Rapid determination of the hydrogen peroxide concentrations is important, because the feedback mechanism of the sterilization process must decide whether enough hydrogen peroxide has been added to sterilize the medical equipment effectively. If not enough hydrogen peroxide has been added to the sterilization chamber, more must be added to allow for acceptable sterilization efficiency. Similarly, if too much hydrogen peroxide has been added or absorbed, the system may abort the run by evacuating the hydrogen peroxide from the chamber, adding plasma to decompose the hydrogen peroxide, or both. One possible alternative for too much peroxide is to open the valve and remove excess hydrogen peroxide from the chamber. The same methods of aborting the method can be used for other sterilants as well.

Although chemical analysis could potentially be used to monitor the hydrogen peroxide concentration in the sterilization chamber, chemical analysis methods are normally too slow to allow for effective monitoring of the hydrogen peroxide concentration to determine whether enough hydrogen peroxide has been added to sterilize the medical equipment effectively. Other, more rapid, monitoring methods for determining the concentration of hydrogen peroxide are therefore preferred over chemical analysis.

Spectrophotometric methods of determining the hydrogen peroxide concentration are preferred over the chemical methods, because the spectrophotometric methods are rapid and give the hydrogen peroxide concentration in real time or nearly so. Although the scope of the method of the invention is not meant to be limited to the analytical technology available today, two forms of spectrophotometric analysis which can presently be used for hydrogen peroxide include analysis with infrared and ultraviolet light. Infrared analysis in the near infrared region, in particular, has been described in the literature. Alternatively, the hydrogen peroxide concentrations in the examples below were determined spectrophotometrically with ultraviolet radiation. Other spectrophotometric methods might also be appropriate for use in various embodiments of the method of the present invention.

The concentration of hydrogen peroxide vapor can also be monitored by measuring the pressure in the chamber.

The pressure in the sterilization chamber can be monitored by a variety of methods. One preferred method of monitoring the pressure is through a pressure transducer.

Semiconductor sensors have also been used to measure the concentration of hydrogen peroxide. The use of the present semiconductor sensors is not a preferred embodiment, because the response time of the sensor is slower than for the other methods. Other rapid methods for analyzing the concentration of hydrogen peroxide on a rapid basis are likely to be developed in the future, and the scope of the method is not meant to be limited by the limitations of the present technology for monitoring the concentration of hydrogen peroxide.

The method can be applied to other sterilants as well by using analytical methods appropriate to the other sterilants.

After the concentration of hydrogen peroxide in the chamber has been determined with the peroxide monitor, it is preferred that the concentration be monitored as a function of time. The concentration of hydrogen peroxide vapor in the sterilization chamber generally decreases with time due to decomposition of the hydrogen peroxide, adsorption or absorption by the surfaces of the sterilization chamber and/or articles in the chamber, reactions with materials in the chamber, etc.

As a result, it is generally preferred that the hydrogen peroxide concentration be monitored as a function of time so that the rate of change in concentration of the hydrogen peroxide can be measured. If the rate of decrease in the concentration is high, more hydrogen peroxide can be added to the chamber. The Examples below include graphs of the concentration of hydrogen peroxide vapor versus time. The effect of equipment load in the chamber causing changes in the concentration of hydrogen peroxide with time will become clearer through the results presented in the Examples. Once again, many factors may affect the efficacy and the material compatibility. The following examples only consider the effect of load.

The first example presents data for a sterilization procedure in which 1 g of 59% hydrogen peroxide was injected into a sterilization chamber with three different loadings of medical equipment. Graphs of hydrogen concentration versus time are presented for the three different loadings. The Example shows how the concentration of hydrogen peroxide in the chamber changes both as a function of time and as a function of the equipment loading in the chamber.

EXAMPLE 1

Effect of the Load On the Concentration of Peroxide with One Gram of 59% Hydrogen Peroxide Each CSR wrapped trays was loaded with the following items:

1 Silicon instrument mat

1 Codman 24-3076 fiberoptic cable 40 pieces of miscellaneous medical devices 1 latex tube with $\frac{1}{8}$" id and $\frac{1}{32}$" wall Each tray with equipment made up one load.

Three different runs were performed with three different loadings, the first with a single load of one tray and equipment, the second with a double load of two trays with equipment, and the third with a triple load of three trays with equipment. The trays and equipment were placed in the 173 liter sterilization chamber, the chamber was evacuated to 0.4 torr, and 1 g of 59% hydrogen peroxide was placed in the vaporizer to generate hydrogen peroxide vapor in the chamber.

The concentration of hydrogen peroxide vapor in the chamber was monitored as a function of time with a ultraviolet spectrophotometer with a deuterium lamp. The spectrophotometer had previously been calibrated by injecting weighed amounts of hydrogen peroxide into the chamber and measuring the absorbance as a function of hydrogen peroxide concentration.

The concentration of hydrogen peroxide in the chamber was then measured as a function of time with the ultraviolet spectrophotometer for the three different loadings, a single load of one tray with medical equipment (shown in FIG. 2), a double load of two trays, each with medical equipment (shown in FIG. 3), and a triple load of three trays, each with medical equipment (shown in FIG. 4).

FIG. 5 shows charts of the concentration of hydrogen peroxide versus time for the three different loadings when 1 g of 59% hydrogen peroxide was injected into the chamber.

The top curve of FIG. 5 shows the concentration of hydrogen peroxide vapor in the chamber for the experiment with a single load of one tray of equipment. The concentration of hydrogen peroxide reached a peak value of about 1.7 mg/L and then declined to a value of about 1.1 mg/L after about 4 minutes.

The middle curve of FIG. 5 shows the hydrogen peroxide concentration as a function of time with a double load of two trays of equipment and 1 g of 59% hydrogen peroxide. The concentration of hydrogen peroxide reached a maximum value of about 1.4 mg/L and subsequently declined to about 0.6 mg/L after about 4 minutes.

The bottom curve of FIG. 5 shows the hydrogen peroxide concentration in the chamber as a function of time with a triple load of three trays of equipment and 1 g of 59% hydrogen peroxide. The maximum concentration of hydrogen peroxide was 1 mg/L, and the concentration decreased to about 0.5 mg/L after about 4 minutes.

Of course, there is no "normal" load of medical equipment. Each load in Example 1 was the same so that the effect of the load could be standardized to the number of standard loads. Each time a sterilization is run, however, the amount of medical equipment will normally vary, depending on what instruments have been used in the operating rooms. Without monitoring the concentration of peroxide in the chamber, one would not know whether enough, too much, or too little peroxide had been injected.

In Example 2, the experiments of Example 1 were repeated, except that 2 g of 59% hydrogen peroxide were injected into the chamber rather than the 1 g of hydrogen peroxide used in Example 1.

EXAMPLE 2

Effect of the Load On the Concentration of Peroxide with Two Grams of 59% Hydrogen Peroxide Three runs with three different loads were performed as in Example 1, except that 2 g of 59% hydrogen peroxide were injected into the chamber rather than the 1 g which was injected in Example 1.

The three runs were performed on the same loads as in Example 1: a single load of one tray of medical equipment; a double load of two trays, each with medical equipment; and a triple load of three trays, each with medical equipment.

The runs were performed as in Example 1, with the exception that 2 grams of 59% hydrogen peroxide were injected, rather than the 1 gram of Example 1.

The concentrations of hydrogen peroxide in the chamber as a function of time for the three different loadings are shown in FIG. 6.

The top curve of FIG. 6 shows the concentration of hydrogen peroxide in the chamber as a function of time with a single load of one tray medical equipment and 2 g of 59% hydrogen peroxide. The highest concentration of hydrogen peroxide in the chamber was about 2.9 mg/L, declining to about 1.8 mg/L after 4 minutes.

The concentration of hydrogen peroxide as a function of time with a double load of two trays of equipment and 2 g of 59% hydrogen peroxide is shown in the middle graph of FIG. 6. In this medium load situation, the peak concentration of the hydrogen peroxide was about 2.5 mg/L, and the concentration declined to 1.2 mg/L after about 4 minutes.

The concentration of hydrogen peroxide in the chamber as a function of time with a heavy load of three trays of equipment and 2 g of 59% hydrogen peroxide is shown in the bottom curve of FIG. 6. The peak concentration of hydrogen peroxide was about 1.8 mg/L, and the concentration fell to about 0.9 mg/L after 4 minutes.

In the following Example, the experiments of Example 1 and 2 were repeated, but 3 grams of 59% hydrogen peroxide were injected into the chamber.

EXAMPLE 3

Effect of the Load On the Concentration of Peroxide with Three Grams of 59% Hydrogen Peroxide The experiments of Examples 1 and 2 were repeated using 3 grams of 59% hydrogen peroxide. As in Examples 1 and 2, experiments were performed with a light load of one tray of instruments, a medium load of two trays of instruments, and a heavy load of three trays of instruments.

The concentration of hydrogen peroxide vapor in the chamber versus time is shown for the three different loadings in FIG. 7. The top plot shows the concentration of hydrogen peroxide versus time for the experiment with the light load of a single tray of instruments. The highest concentration of hydrogen peroxide which was observed was about 3.4 mg/L. The hydrogen peroxide concentration decreased to about 2.4 mg/L after 4 minutes.

The middle chart of FIG. 7 shows the concentration of hydrogen peroxide vapor versus time for the medium load of two trays of instruments. The highest concentration of hydrogen peroxide which was observed was about 2.6 mg/L, and the concentration decreased to about 1.6 mg/L after 4 minutes.

The bottom curve of FIG. 7 shows the concentration of hydrogen peroxide vapor versus time for the experiment with a high load of three trays of instruments. The highest concentration of hydrogen peroxide which was observed was about 2.2 mg/L, and the concentration decreased to about 1.3 mg/L after 4 minutes.

The results of the effect of the load are summarized in Table 1 below.

TABLE 1

Concentration of Peroxide in the Chamber During the First Four Minutes

| | | Peroxide Concentration (mg/L) | |
| --- | --- | --- | --- |
| | | Maximum | Minimum |
| 1 gram | 1 Tray | 1.7 | 1.1 |
| of 59% | 2 Trays | 1.4 | 0.6 |
| Peroxide | 3 Trays | 1.0 | 0.5 |
| 2 grams | 1 Tray | 2.9 | 1.8 |
| of 59% | 2 Trays | 2.5 | 1.2 |
| Peroxide | 3 Trays | 1.8 | 0.9 |
| 3 grams | 1 Tray | 3.4 | 2.4 |
| of 59% | 2 Trays | 2.6 | 1.6 |
| Peroxide | 3 Trays | 2.2 | 1.3 |

It is easy to conclude from the results that the concentration of hydrogen peroxide in the chamber increases as the amount of peroxide increases and decreases with an increase in the load. It is difficult to define the minimum peroxide required to achieve good efficacy, because the exposure temperature, cycle time, and the device to be sterilized also affect the efficacy of the process. For example, it requires more peroxide, higher temperatures, or longer exposure to sterilize the interior of a lumen device than to sterilize the exterior of the lumen device. Lumens with different dimensions require different sterilization conditions. Devices that absorb peroxide need more peroxide to sterilize than the devices that do not absorb peroxide. Also, the efficacy with low peroxide concentrations can be compensated with higher temperature or longer exposure times. Therefore, the amount of peroxide required for good efficacy is dependent on the process parameters and the load to be sterilized.

If the minimum concentration of peroxide required to achieve good sterilization efficacy for the above examples is 1.0 mg/L after four minutes diffusion or 1.5 mg/L at the peak, then one gram of 59% peroxide is not enough to sterilize two or three trays in the chamber. Also, two grams of 59% peroxide is not enough to sterilize three trays. More peroxide would improve the efficacy of the sterilization.

Likewise, if the maximum concentration of peroxide for having acceptable residues and material compatibility is less than 1.5 mg/L after four minutes diffusion or 2.5 mg/L at the peak, then three grams of 59% peroxide is too much for one or two trays. Also, two grams of 59% peroxide is too much for one tray in the chamber. Less peroxide is better for the medical device.

Apparently, there is a need to balance good sterilization efficacy and acceptable material compatibility. Different amounts of hydrogen peroxide are optimal for different loads in the sterilization chamber. By monitoring the concentration of hydrogen peroxide in the chamber for different loads, one can determine whether an optimal amount of hydrogen peroxide has been injected into the sterilization chamber.

FIG. 8A is a block diagram showing the number of trays of instruments in the various experiments, the number of grams of 59% hydrogen peroxide added, the efficiency of sterilization, and the material compatibility. The most desirable situation is "More acceptable efficacy and material compatibility". If the concentration of hydrogen peroxide was not high enough to effectively sterilize the instruments, the section is labeled as "Less acceptable efficacy". If the concentration of hydrogen peroxide was high enough to potentially damage the medical instruments, the block is labeled as "Less acceptable material compatibility".

With a light load of one tray, 1 gram of 59% hydrogen peroxide was "More acceptable efficacy and material compatibility". If 2 or 3 grams of 59% hydrogen peroxide were used, there was potential damage to the medical instruments, or too much residual could be left on the devices, and the conditions were in the region of "Less acceptable material compatibility".

With a medium load of two trays of medical instruments, 1 gram of 59% hydrogen peroxide was not effective at sterilization. The experiment was in the region of "Less acceptable efficacy". Two grams of 59% hydrogen peroxide provided a good balance of sterilization and material compatibility and was in the region of "More acceptable efficacy and material compatibility". Three grams of 59% hydrogen peroxide was too much hydrogen peroxide for the medium load of 2 trays of instruments, and the experiment was in the region of "Less acceptable material compatibility", where the instruments might be damaged by the hydrogen peroxide, or too much residual could be left on the instruments.

Finally, with a heavy load of three trays of medical instruments, 1 and 2 grams of 59% hydrogen peroxide were too small an amount to effectively sterilize the instruments, and both experiments were in the region of "Less acceptable efficacy". When 3 grams of 59% hydrogen peroxide were injected with the heavy load, there was a good balance between sterilization efficiency and material compatibility. The experiment was in the region of "More acceptable efficacy and material compatibility".

Thus, each of the load levels required a different amount of hydrogen peroxide to effectively sterilize the instruments without having a level of hydrogen peroxide which was so high that the instruments might be damaged or have too much residual. There are a great number of factors which determine how much hydrogen peroxide is required to be in the region of "More acceptable efficacy and material compatibility".

The difficulty of determining the appropriate amount of hydrogen peroxide which is required to sterilize a given load is especially important for larger sterilization chambers, because the equipment load can vary much more than for a small sterilizer, because much more equipment can be placed in a large sterilizer than a small sterilizer. With the larger volume of equipment in the large sterilizer, there is much more potential in under- or overestimating the amount of sterilant which is required to sterilize the equipment. If enough hydrogen peroxide is introduced into the sterilization chamber to treat the worst case, then the amount of sterilant which is introduced could be too much for the light load which might be present. The excess sterilant might damage the medical equipment or leave too much residual on the medical devices. Also, if the load is greater than the worst case load, a long abort cycle would be required. Once again, many factors may affect the efficacy and the material compatibility. The following examples only consider the effect of load.

Figure 8B:
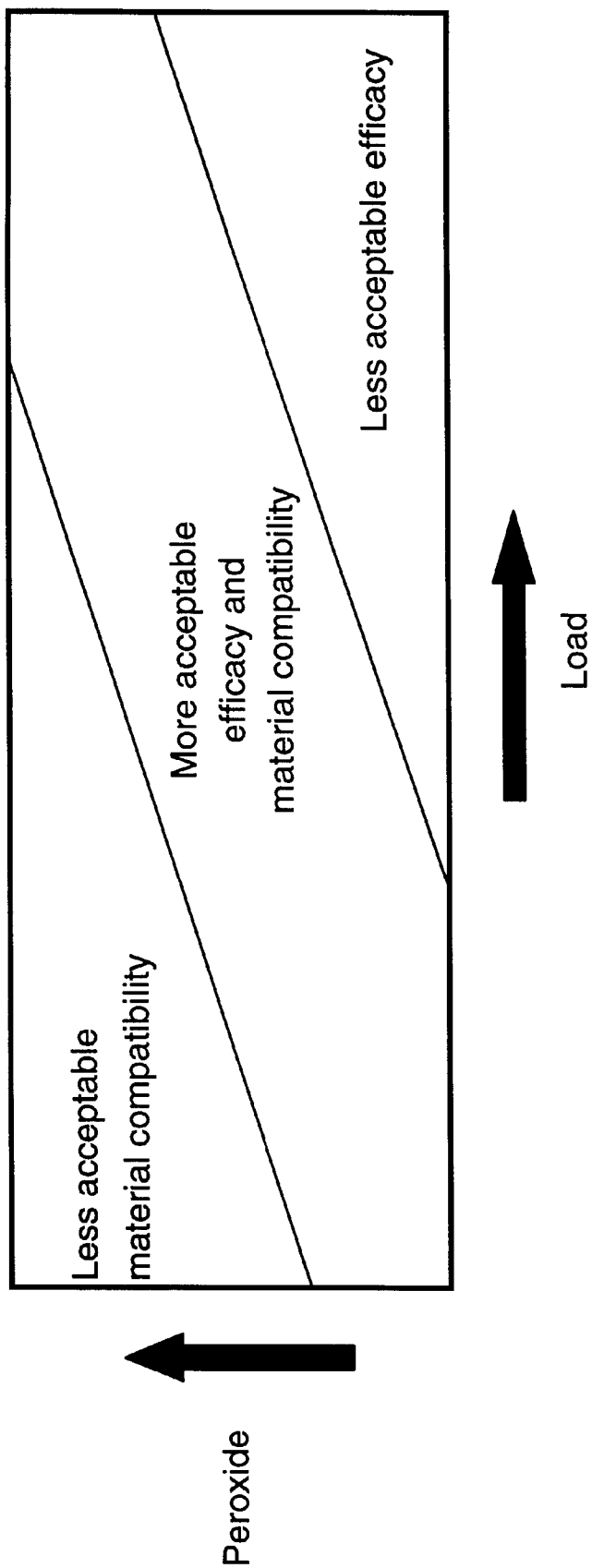
FIG. 8B is a chart of concentration of peroxide versus load showing regions of acceptable and less acceptable material compatibility and sterilization efficacy.

FIG. 8B provides another view of the effect of load and peroxide concentration on the efficacy and material compatibility. In general, the amount of peroxide used for sterilization should depend on the load in the chamber. A feedback mechanism is needed in order to introduce the appropriate amount of sterilant into the chamber and to obtain the best efficacy and material compatibility.

Figure 9:
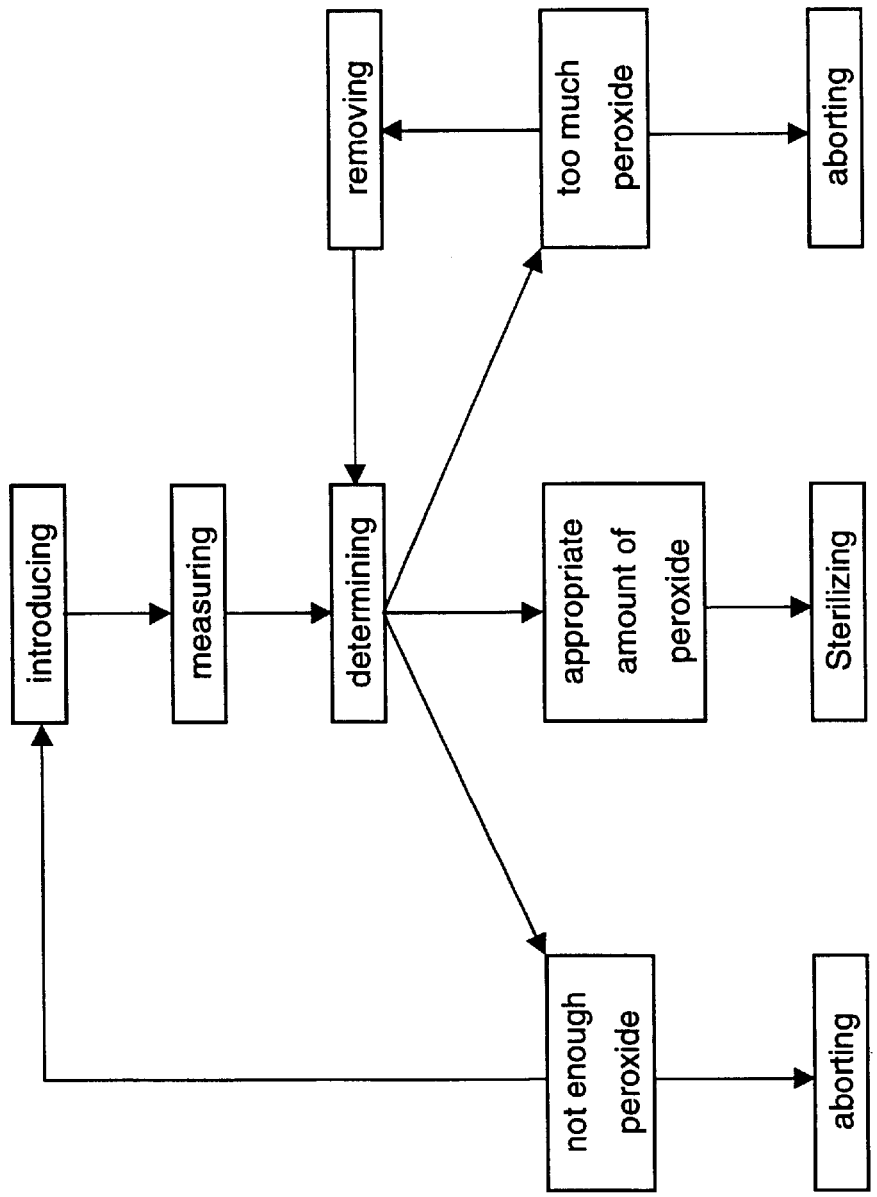
FIG. 9 is a flow chart for conducting a sterilization with various embodiments of the invention.

FIG. 9 shows a flow chart illustrating the method for determining the amount of hydrogen peroxide to add to a sterilizer. The following steps are performed to determine the amount of hydrogen peroxide for the load in the sterilization chamber.

1. An initial amount of sterilant is delivered into the sterilization chamber, and the concentration of hydrogen peroxide is monitored. If too much sterilant has been added, the sterilization is aborted. Another option for too much sterilant is to open the valve and remove excess peroxide from the chamber.
2. If the initial amount of sterilant is enough to sterilize the load but not so much as to damage the equipment, the sterilization cycle is continued.
3. If the initial amount of sterilant is not enough to sterilize the load, more sterilant is added. If the peroxide signal is lower than an acceptable level due to absorbent materials, the cycle can be aborted. Preferably a microprocessor is used to estimate how much more sterilant is required to sterilize the load, based on the concentration of hydrogen peroxide vapor in the sterilization chamber, the rate of decline in the concentration, and the amount of hydrogen peroxide added initially. If necessary, the sterilant can be added in increments and the concentration of sterilant monitored as the incremental amounts of hydrogen peroxide.

As more data are obtained on the response of the sterilization system to added sterilant, the algorithms in the microprocessor can be updated and refined so that the number of cycles of adding additional sterilant can be minimized.

The response of each sterilization load to additional sterilant varies, because the amount of equipment changes almost every time a sterilization is done, and each load will probably have contain different materials. By building a database of the decline in concentration of the hydrogen peroxide with time for different load levels and load compositions, a database can be built to improve the algorithm for use in a microprocessor to minimize the number of times that incremental amounts of hydrogen peroxide must be added.

Source of Sterilant

The sterilant can be added as a small amount from a reservoir. If the source of sterilant is a reservoir, the addition can be metered fairly precisely, because the addition does not need to be of a certain size.

Alternatively, the addition of the sterilant may be from one or more cells from a cassette. If a cassette is used, the amount of the sterilant addition is determined by the size of the cells of the cassette. Normally it is not possible to add, for example, only half of a cell.

Amount of Initial Sterilant

There are many methods which can be used to determine the initial amount of sterilant. First, just enough sterilant can be introduced to produce a detectable signal. The size of the initial signal and the decline in the signal can then be monitored to determine how much, if any, additional sterilant should be added.

The second method is to initially introduce just enough sterilant to sterilize a reasonable light load. The change in concentration of sterilant versus time can be monitored with the peroxide monitor. By monitoring the shape of the decline curve, a determination can be made of how much, if any, additional peroxide is needed for optimal sterilization. The determining can be made at the maximum of the curve, at the minimum after four minutes, by the rate of change from the maximum to the minimum, or by the rate of change from the initial to the maximum. If more hydrogen peroxide is needed, the additional amount of hydrogen peroxide can be introduced into the sterilization chamber. Preferably, the concentration of hydrogen peroxide is monitored after the additional hydrogen peroxide is introduced in the event that further adjustments need to be made.

In the third method, an amount less than or equal to 50% of the amount needed to sterilize a fill load is vaporized.

In the fourth method, an amount of sterilant which produces a pressure in the chamber less than the vapor pressure of the sterilant is vaporized.

Determining the Load

The load can be determined in a variety of ways.

1. The load can be determined based on the maximum in a parameter related to the concentration of sterilant in the chamber.
2. The load can be determined based on the minimum in the parameter. In the experiments in the examples, the minimum was measured four minutes after the sterilant was introduced into the chamber. Four minutes is an arbitrary time, and other time periods could be used instead.
3. The load can be determined based on the rate of change in the parameter from the maximum to the minimum.

Other methods of determining the load can be used without departing from various embodiments of the invention.

Additional Sterilant

If additional sterilant is needed, it can be introduced all at once from a reservoir. Alternatively, it can be introduced cell by cell from a cassette.

Although the discussion focussed on the use of peroxide as a sterilant, the method is also applicable to other sterilants such as ethylene oxide and peracetic acid.

Advantages of the Method

The various embodiments of the method of the invention have several advantages over other methods of sterilization.

1. Only the needed amount of sterilant is introduced into the sterilizer. The chances of damaging the medical devices with excess sterilant or leaving a residual on the equipment are therefore minimized.
2. The user can start the cycle regardless of the load without wasting sterilant. With conventional methods, the user normally waits until a full load is in the sterilizer, because the same amount of sterilant will be used, regardless of the load in the chamber.
3. The residual sterilant on the devices is minimized, because the amount of excess sterilant is minimized.
4. More cycles can be conducted with a given cassette or reservoir, because the amount of sterilant used in each cycle is minimized.
5. The abort cycle can be detected with a minimal amount of sterilant.

The system can determine with a high degree of certainty whether the cycle will have to be aborted after the initial amount of sterilant is placed in the sterilization chamber.

While embodiments and applications of this invention have been shown and described, it should be apparent to those skilled in the art that many more modifications are possible without departing from the scope of the invention. The invention is therefore not to be restricted, except in the spirit of the appended claims.

What is claimed is:

1. A method of determining and sterilizing a load in a sterilization chamber comprising:

(a) introducing a known amount of sterilant into said sterilization chamber, wherein said sterilant has a vapor pressure and wherein said known amount of sterilant is less than or equal to 50% of an amount to sterilize a fully loaded chamber;

(b) measuring a parameter related to a concentration of sterilant in said sterilization chamber, wherein said measuring is during or after introducing;

(c) determining the load in said sterilization chamber from said concentration of sterilant in said sterilization chamber, wherein said determining is during or after measuring;

(d) repeating steps (a) to (c), if necessary; and (e) sterilizing said load.

2. The method of claim 1, wherein said known amount of sterilant is an amount of sterilant which produces a pressure in said chamber less than the vapor pressure of said sterilant.

3. The method of claim 1, wherein said known amount of sterilant is introduced from a reservoir of sterilant.

4. The method of claim 1, wherein said known amount of sterilant is introduced from a cassette.

5. The method of claim 4, wherein said known amount of sterilant is introduced from at least one cell in the cassette.

6. The method of claim 1, wherein said parameter is measured over a time period, wherein said time period is the time during said determining.

7. The method of claim 6, wherein said determining is based on a maximum of said parameter in said time period.

8. The method of claim 6, wherein said determining is based on a minimum of said parameter in said time period.

9. The method of claim 8, wherein the minimum of said parameter in said time period is measured within four minutes after introducing said known amount of sterilant into said chamber.

10. The method of claim 6, wherein said determining is based on a rate of change of said parameter in said time period from a maximum to a minimum of said parameter.

11. The method of claim 10, wherein said determining is based on a rate of change of said parameter in said time period from a maximum to a minimum in said parameter measured within four minutes after introducing said known amount of sterilant into said chamber.

12. The method of claim 6, wherein said determining is based on a rate of change of said parameter in said time period from an initial time to a maximum in said parameter.

13. The method of claim 1, wherein said sterilant comprises a source of hydrogen peroxide.

14. The method of claim 13, wherein said source of hydrogen peroxide comprises a liquid solution or a solid peroxide complex.

15. The method of claim 1, wherein said concentration of sterilant is measured by a method selected from the group consisting of spectrophotometric methods, measuring a pressure in the sterilization chamber, and measuring with a semiconductor sensor.

16. The method of claim 1, wherein the parameter related to the concentration of sterilant is measured by a spectrophotometric method in the infrared or ultraviolet region.

17. The method of claim 1, additionally comprising exposing said load to plasma.

18. The method of claim 17, wherein said method is performed within a sealed chamber and said plasma is generated within said chamber.

19. The method of claim 17, wherein said method is performed within a first chamber and said plasma is generated in a second, separate chamber and said method further comprises the step of flowing said plasma into said first chamber.

20. The method of claim 1, wherein said known amount of sterilant is more than an amount of sterilant required to sterilize said load.

21. The method of claim 20, further comprising removing at least a portion of the sterilant with vacuum.

22. The method of claim 1, further comprising aborting the method.

23. The method of claim 22, wherein aborting the method comprises removing at least a portion of the sterilant with vacuum.

24. The method of claim 22, wherein aborting the method comprises decomposing at least a portion of the sterilant with plasma.

25. The method of claim 1, wherein said determining the load is based on the concentration of sterilant.

26. A method of determining and sterilizing a load in a sterilization chamber comprising:
  (a) introducing a known amount of sterilant into said sterilization chamber, wherein said sterilant has a vapor pressure and wherein said known amount of sterilant is more than an amount of sterilant required to sterilize said load;
  (b) measuring a parameter related to a concentration of sterilant in said sterilization chamber, wherein said measuring is during or after introducing;
  (c) determining the load in said sterilization chamber from said concentration of sterilant in said sterilization chamber;
  (d) removing at least a portion of the sterilant with vacuum;
  (e) repeating steps (b) to (d) if necessary; and
  (f) sterilizing said load, wherein said removing is before said sterilizing.

* * * * *